US010465189B2

(12) United States Patent
Venkatraman et al.

(10) Patent No.: US 10,465,189 B2
(45) Date of Patent: Nov. 5, 2019

(54) MULTILAYERED NANOPARTICLE AND METHODS OF MANUFACTURING AND USING THE SAME

(71) Applicants: NANYANG TECHNOLOGICAL UNIVERSITY, Singapore (SG); SINGAPORE HEALTH SERVICES PTE LTD, Singapore (SG)

(72) Inventors: Subramanian Venkatraman, Singapore (SG); Tzee Ling Tina Wong, Singapore (SG); Bjorn Neu, Singapore (SG)

(73) Assignees: NANYANG TECHNOLOGICAL UNIVERSITY, Singapore (SG); SINGAPORE HEALTH SERVICES PTE LTD, Singapore (SG)

( * ) Notice: Subject to any disclaimer, the term of this patent is extended or adjusted under 35 U.S.C. 154(b) by 0 days.

(21) Appl. No.: 15/104,123

(22) PCT Filed: Dec. 9, 2014

(86) PCT No.: PCT/SG2014/000587
§ 371 (c)(1),
(2) Date: Jun. 13, 2016

(87) PCT Pub. No.: WO2015/088445
PCT Pub. Date: Jun. 18, 2015

(65) Prior Publication Data
US 2016/0319280 A1 Nov. 3, 2016

Related U.S. Application Data

(60) Provisional application No. 61/915,790, filed on Dec. 13, 2013.

(51) Int. Cl.
| | | |
|---|---|---|
| *C12N 15/113* | (2010.01) | |
| *A61K 31/713* | (2006.01) | |
| *A61K 48/00* | (2006.01) | |
| *C12N 15/11* | (2006.01) | |
| *A61K 9/50* | (2006.01) | |
| *A61K 9/51* | (2006.01) | |

(52) U.S. Cl.
CPC ............ *C12N 15/113* (2013.01); *A61K 9/501* (2013.01); *A61K 9/5036* (2013.01); *A61K 9/5052* (2013.01); *A61K 9/5078* (2013.01); *A61K 9/5089* (2013.01); *A61K 31/713* (2013.01); *A61K 48/0041* (2013.01); *C12N 15/111* (2013.01); *A61K 9/5107* (2013.01); *C12N 2310/14* (2013.01); *C12N 2320/32* (2013.01)

(58) Field of Classification Search
CPC ...... C12N 15/113; A61K 9/5052; C12Q 1/68; C07H 21/04
See application file for complete search history.

(56) References Cited

U.S. PATENT DOCUMENTS

| | | | |
|---|---|---|---|
| 8,440,625 B2* | 5/2013 | Tai .................. | C07K 14/47 514/1.1 |
| 2012/0244224 A1 | 9/2012 | Biris et al. | |
| 2012/0321573 A1* | 12/2012 | Karp ................... | A61K 9/0014 424/59 |
| 2013/0095187 A1 | 4/2013 | Hahn et al. | |

FOREIGN PATENT DOCUMENTS

| | | |
|---|---|---|
| WO | 2009/058913 A2 | 5/2009 |
| WO | 2011/043739 A1 | 4/2011 |
| WO | 2012/075241 A2 | 6/2012 |
| WO | 2013/163234 A1 | 10/2013 |
| WO | WO2013/163234 | * 10/2013 |

OTHER PUBLICATIONS

Lee et al, Effective Gene Silencing by Multilayered siRNA Coated Gold Nanoparticles, 2011, Small, 7, 364-370. (Year: 2011).*
Shi et al, Targeting SPARC expression decreases glioma cellular survival and invasion associated with reduced activities ofFAK and ILK kinases, 2007, Oncogene, 26, 4084-4094. (Year: 2007).*
Data sheet SEQ ID No. 1 search results from patent data base, 2018, pp. 1-10, printed on Jan. 25, 2018 (Year: 2018).*
Data sheet SEQ ID No. 2 search results from patent data base, 2018, pp. 1-10, printed on Jan. 25, 2018 (Year: 2018).*
Klesing et al, Freeze-dried cationic calcium phosphate nanorods as versatile carriers of nucleic acids (DNA, siRNA), 2012, J. Mater. Chem., 2012, 22, 199-204. (Year: 2012).*
Hossain et al , Carbonate apatite-facilitated intracellularly delivered siRNA for efficient knockdown of functional genes, 2010, Journal of Controlled Release, 147, 101-108 (Year: 2010).*
Park, Carbonate apatite-facilitated intracellular delivery of siRNA, 2010, Journal of Controlled Release, 147, 1 (Year: 2010).*
STIC search results for SEQ ID No. 2, printed on Nov. 17, 2018. pp. 1-11 (Year: 2018).*
STIC search results for SEQ ID No. 1, printed on Nov. 17, 2018. pp. 1-12 (Year: 2018).*
Deng et al., "Layer-by-Layer Nanoparticles for Systemic Codelivery of an Anticancer Drug and siRNA for Potential Triple-Negative Breast Cancer Treatment," *ACS Nano* 7(11):9571-9584, 2013.
Donath et al., "Novel Hallow Polymer Shells by Colloid-Templated Assembly of Polyelectrolytes," *Angew. Chem. Int. Ed.* 37(16):2201-2205, 1998.
Guo et al., "Engineering RNA for Targeted siRNA Delivery and Medical Application," *Advanced Drug Delivery Reviews* 62:650-666, 2010.
Kapoor et al., "Physicochemical characterization techniques for lipid based delivery systems for siRNA," *International Journal of Pharmaceutics* 427:35-57, 2012.
Lee et al., "Effective Gene Silencing by Multilayered siRNA-Coated Gold Nanoparticles," *small* 7(3):364-370, 2011.

(Continued)

*Primary Examiner* — Narayan K Bhat
(74) *Attorney, Agent, or Firm* — Seed IP Law Group LLP

(57) ABSTRACT

The invention relates to a multilayered nanoparticle for delivery of RNA to a cell and methods of manufacturing and using the same. The multilayered nanoparticle has a core nanoparticle coated by alternating positively and negatively charged polymer layers, wherein the at least one of the negatively charged polymer layers is RNA.

18 Claims, 9 Drawing Sheets

Specification includes a Sequence Listing.

(56) References Cited

OTHER PUBLICATIONS

Seet et al., "*In vitro* analyses of the anti-fibrotic effect of SPARC silencing in human Tenon's fibroblasts: comparisons with mitomycin C," *J Cell. Mol. Med.* 16(6):1245-1259, 2012.

Seet et al., "SPARC Deficiency Results in Improved Surgical Survival in a Novel Mouse Model of Glaucoma Filtration Surgery," *Plos ONE* 5(2):e9415, 2010. (13 pages).

Tan et al., "Engineering Nanocarriers for siRNA Delivery," *small* 7(7):841-856, 2011.

Tan et al., "Layer-by-Layer Nanoparticles as an Efficient siRNA Delivery Vehicle for SPARC Silencing," *small* 10(9):1790-1798, 2014.

Whitehead et al., "Knocking down barriers: advances in siRNA delivery," *Nature Reviews Drug Discovery* 8:129-138, 2009.

Rongcong, Luo et al. "*Surface Functionalization of Nanoparticles to Control Cell Interactions and Drug Releases*", SMALL, Aug. 20, 2012; pp. 2585-2594.

Extended European Search Report, dated Jun. 19, 2017, for corresponding European Patent Application No. 14870520.5, 8 pages.

Lee et al., "A Fabricated siRNA Nanoparticle for Ultralong Gene Silencing in Vivo," *Adv.Funct. Mater.* 23:3488-3493, 2013.

Malhotra et al., "Development and characterization of chitosan-PEG-TAT nanoparticles for the intracellular delivery of siRNA," *International Journal of Nanomedicine* 8:2041-2052, 2013.

Rai et al., "Combining Chemistry and Biology to Create Colloidally Stable Bionanohydroxyapatite Particles: Toward Load-Bearing Bone Applications," *Langmuir* 24:7744-7749, 2008.

Oshima, "Chapter 5: Organ Function—Engineering one organ," *Primer for Medical Engineering: Engineering to Support Medicine*, p. 162, 2008. (4 pages, including machine translation).

\* cited by examiner

A.

Coating of first polyelectrolyte on HA nanoparticle

Coating of second polyelectrolyte

Coating of siGLO Green siGLO Green encapsulated within polyelectrolyte multilayer

B.

| Layer-*by*-Layer nanoparticles | Mean particle size (nm) | Dispersity ± SD | Zeta potential (mV ± SD) |
|---|---|---|---|
| HA | 121 ± 5 | 0.23 ± 0.01 | -22 ± 1 |
| HA/ARG/ | 230 ± 54 | 0.2 ± 0.04 | 57.5 ± 8.3 |
| HA/ARG/DXS/ | 245 ± 20 | 0.2 ± 0.08 | -63.3 ± 10.7 |
| HA/ARG/DXS/ARG/ | 347 ± 44 | 0.3 ± 0.09 | 43.1 ± 13.5 |
| HA/ARG/DXS/ARG/SPARC/ | 375 ± 107 | 0.3 ± 0.07 | -35.6 ± 8.1 |
| HA/ARG/DXS/ARG/SPARC/ARG/ | 350 ± 94 | 0.3 ± 0.23 | 43.9 ± 9.8 |

D

A

B

SEQUENCE LISTING

```
<160> NUMBER OF SEQ ID NOS: 8

<210> SEQ ID NO 1
<211> LENGTH: 21
<212> TYPE: RNA
<213> ORGANISM: Artificial Sequence
<220> FEATURE:
<223> OTHER INFORMATION: SiRNA sense sequence

<400> SEQUENCE: 1
aacaagaccu ucgacucuuu c                                              21
```

```
<210> SEQ ID NO 2
<211> LENGTH: 21
<212> TYPE: RNA
<213> ORGANISM: Artificial Sequence
<220> FEATURE:
<223> OTHER INFORMATION: SiRNA antisense sequence

<400> SEQUENCE: 2
ggaagagucg aaggucuugu u                                              21

<210> SEQ ID NO 3
<211> LENGTH: 21
<212> TYPE: RNA
<213> ORGANISM: Artificial Sequence
<220> FEATURE:
<223> OTHER INFORMATION: scrambled siRNA sense sequence

<400> SEQUENCE: 3
gcucacagcu caauccuaau c                                              21

<210> SEQ ID NO 4
<211> LENGTH: 21
<212> TYPE: RNA
<213> ORGANISM: Artificial Sequence
<220> FEATURE:
<223> OTHER INFORMATION: scrambled siRNA antisense sequence

<400> SEQUENCE: 4
gauuaggauu gagcugugag c                                              21

<210> SEQ ID NO 5
<211> LENGTH: 22
<212> TYPE: DNA
<213> ORGANISM: Artificial Sequence
<220> FEATURE:
<223> OTHER INFORMATION: forward primer for 60S ribosomal protein L13'

<400> SEQUENCE: 5
catcgtggct aaacaggtac tg                                             22

<210> SEQ ID NO 6
<211> LENGTH: 20
<212> TYPE: DNA
<213> ORGANISM: Artificial Sequence
<220> FEATURE:
<223> OTHER INFORMATION: reverse primer for 60S ribosomal protein L13'

<400> SEQUENCE: 6
gcacgacctt gagggcagcc                                                20

<210> SEQ ID NO 7
<211> LENGTH: 20
<212> TYPE: DNA
<213> ORGANISM: Artificial Sequence
<220> FEATURE:
<223> OTHER INFORMATION: SPARC gene Forward primer

<400> SEQUENCE: 7
gtgcagagga aaccgaagag                                                20

<210> SEQ ID NO 8
<211> LENGTH: 20
<212> TYPE: DNA
<213> ORGANISM: Artificial Sequence
<220> FEATURE:
```

```
<223> OTHER INFORMATION: SPARC gene reverse primer

<400> SEQUENCE: 8
tgtttgcagt ggtggttctg                                              20
```

MULTILAYERED NANOPARTICLE AND METHODS OF MANUFACTURING AND USING THE SAME

CROSS REFERENCE

This application claims the benefit of priority of U.S. Provisional Patent Application No. 61/915,790 filed Dec. 13, 2013, the contents of which being hereby incorporated by reference in its entirety for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_505USPC_SEQUENCE_LISTING.txt. The text file is 2.1 KB, was created on Jun. 13, 2016, and is being submitted electronically via EFS-Web.

FIELD OF THE INVENTION

The present invention relates to nanoparticles for delivering RNA to cells and organisms and methods of manufacturing and using the same.

BACKGROUND OF THE INVENTION

Ribonucleic acid (RNA) is a nucleic acid molecule that, unlike double-stranded DNA that contains deoxyribose, is mostly single-stranded and contains ribose. RNA is inherently less stable than DNA because it is more prone to hydrolysis. This makes it very difficult to deliver RNA to a cell or an organism as it is easily broken down, rendering it biologically inactive.

Ribonucleases are enzymes that catalyze the degradation of RNA. Ribonucleases are extremely common in all cells, resulting in very short lifespans for any RNA that is not in a protected environment. Natural mechanisms have developed to protect RNA from ribonucleases including 5' end capping, 3' end polyadenylation, folding within an RNA protein complex, and ribonuclease inhibitor (RI). Nevertheless, the delivery of RNA to cells or organisms is greatly complicated by the presence of ubiquitous and hardy ribonucleases that degrade RNA, making it very difficult to deliver RNA to cells. Currently, RNA is mostly delivered to cells via DNA encoding said RNA, e.g. in form of vectors, so that the RNA is synthesized in situ within the cell. However, this approach requires a range of control, selection and detection molecules that need to be introduced to the cell as well. Such additional molecules complicate the production and are not always desirable due to cell toxicity concerns.

The problems connected to RNA delivery have escalated with 'RNA interference' (RNAi)—a genetic expression control mechanism first discovered by Fire, Mello and co-workers in the late 1990s. RNAi refers to the specific down-regulation of proteins in target cells or organs. To use such RNAi in gene therapy there is a need to deliver the RNAi to cells.

Similarly, gene expression of a multitude of undesired proteins in a cell can be altered through post-transcriptional gene silencing achieved by the introduction of small interfering RNA (siRNA) molecules into the cytoplasm of the cell.

siRNA, a double stranded 21-23 nucleotides RNA duplex having complementarity to a target mRNA, is separated the single strands, the so-called passenger strand and guide strand. While the passenger strand is degraded, the guide strand is incorporated into the RNA-induced silencing complex (RISC), binds it complementary mRNA and prevents translation thereof by means of RNAse (argonaute) activation. Due to its simplicity and the low-dose effect, RNAi can be regarded as a promising tool for an elegant, curative treatment of a wide range of diseases.

Various approaches have been reported for delivering siRNA into the cytoplasm, such as polymeric nanoparticles (NPs), liposomes and surface modifications by folate, cholesterol, biotin or fluorescent molecules (Guo et al., Adv. Drug Del. Rev. 2010, 62, 650; Kapoor et al., Int J Pharm, 2012, 427, 35; and Tan et al., Small 2011, 7, 841.)

To improve gene silencing efficiency, viral vectors have been utilized for siRNA delivery as well. Nevertheless, overcoming viral vector oncogenicity and immunogenicity remains a significant barrier for viral-based siRNA delivery (Whitehead et al., Nat. Rev. Drug Discov. 2009, 8, 129.). The poor cellular uptake of naked siRNA, its rapid degradation by RNAses and the difficulty of targeting of siRNA to systemic disease sites are currently limiting the widespread use of siRNA therapeutics (Guo et al., 2010). To overcome this, lipid or polymer-based siRNA delivery systems have been successfully used for local siRNA delivery, particularly to ocular, intradermal, liver, neural, pulmonary targets. In addition to effective cellular uptake, non-toxicity/non-immunogenicity of the carriers and effective intracellular delivery of siRNA are essential for RNAi to function as therapeutics. Therefore, current research focuses on non-viral vectors, such as polymer-based nanoparticles to overcome these challenges. However, most non-viral carriers lack acceptable efficacy and possess a high level of cytotoxicity (Tan et al., 2011).

Consequently, efficient and safe delivery systems for siRNA therapeutics remain a challenge.

The layer-by-layer (LbL) self assembly of polycations and polyanions on colloids was first described by Donath et al. (Angew. Chem. Int. Ed. Engl. 1998, 37, 2201.). The gentle assembly based on electrostatic interactions between positively and negatively charged polymers is a simple and versatile method with high applicability. Former studies focused on micro/nanoparticles such as polystyrene latex, silica and melamine formaldehyde and more biocompatible templates, such as calcium carbonate, poly(D,L-lactide-co-glycolide) (PLGA) flat templates, as well as biological cells.

Secreted protein, acidic and rich in cysteine (SPARC; also called osteonectin) is a calcium-binding extracellular matrix glycoprotein that modulates the interaction between the cell and the extracellular matrix and cell migration. There is a strong association between elevated expression of SPARC and tissue scarring and fibrosis. Increased expression of SPARC has been observed in fibrotic disorders and targeting of SPARC expression to modulate fibrosis has been evaluated as a potential therapeutic approach.

Fibrosis, which is the secretion and deposition of the cell extracellular matrix (ECM), is a frequent result of various diseases such as hypertension, diabetes, liver cirrhosis and inflammatory processes. In fibrosis, there is elevated SPARC expression indicating the involvement of the SPARC protein in modulating ECM interactions. SPARC expression and up-regulation has been reported in multiple types of fibrosis, both in human tissues and animal models. Researchers have shown that inhibition of SPARC expression decreases fibrosis involving dermal, hepatic, renal, pulmonary, intestinal fibrosis and glaucoma. Seet et al (*PLoS One,* 2010, 5, 9415), reported that the reduction of SPARC improved surgical success in a surgical mouse model of ocular scarring. Hence, the targeting of SPARC expression has been identified as a potential therapeutic strategy for wound modulation and reducing scarring since SPARC down-regulation also resulted in delayed cell migration, reduced collagen contractility and lower expressions of profibrotic and pro-inflammatory genes (Seet et al., *J. Cell. Mol. Med.* 2012, 16, 1245).

Elevated secreted protein, acidic and rich in cysteine (SPARC) protein expression is associated with tissue scarring and fibrosis, while inhibition of SPARC can reduce scarring. siRNA targeted at the SPARC gene is therefore a promising way to inhibit SPARC and reduce scarring. The challenge is to deliver bioactive SPARC siRNA to an injury site.

SUMMARY OF THE INVENTION

The present invention meets the need for methods for the delivery of intact RNA to a target site by providing, in a first aspect of the invention, a multilayered nanoparticle for delivery of RNA to a cell, the nanoparticle comprising: a core nanoparticle coated by alternating positively and negatively charged polymer layers, wherein the number of layers is 2 or more and wherein at least one of the negatively charged polymer layers comprises or consist of RNA.

Another aspect of the invention relates to a method for manufacturing the multilayered nanoparticle as described herein, comprising the steps of: a) Providing a nanoparticle core; b) Contacting the nanoparticle core with a positively charged or negatively charged polymer to form a first polymer layer on the nanoparticle core; c) Contacting the coated nanoparticle of step b) with a polymer charged opposite to that used in step b) to form a second polymer layer on the nanoparticle; d) Optionally repeating steps b) and c), wherein at least one of the negatively charged polymer layers comprises or consist of RNA.

Another aspect of the invention relates to a method for the delivery of RNA (siRNA) to a cell or organism comprising: contacting said cell or organism with an effective amount of the multilayered nanoparticle as described herein.

A further aspect of the invention relates to a method for the treatment of an RNA-treatable disease or disorder in a subject, comprising administering an effective amount of the multilayered nanoparticle as described herein to the subject.

A still further aspect of the invention is directed to the use of the multilayered nanoparticle as described herein for the delivery of an RNA to a cell or organism.

Also encompassed by the invention are multilayered nanoparticles as described herein for use in the treatment of RNA-treatable diseases or disorders.

Other aspects of the invention will be apparent to a person skilled in the art with reference to the following drawings and description of various non-limiting embodiments.

BRIEF DESCRIPTION OF THE DRAWINGS

The drawings are not necessarily drawn to scale, emphasis instead generally being placed upon illustrating the principles of various embodiments. In the following description, various embodiments of the invention are described with reference to the following drawings.

DETAILED DESCRIPTION

Figure 1:
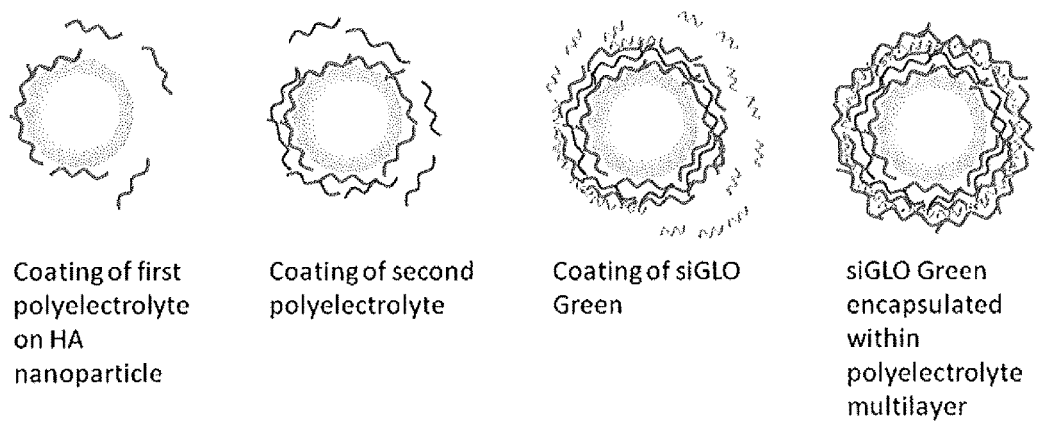
FIG. 1. Schematic illustration of A. the manufacture of the multilayered nanoparticle according to one embodiment of the invention and B. the delivery of RNA to a cell via defoliation of the multilayered nanoparticle in the cells.
Figure 1:
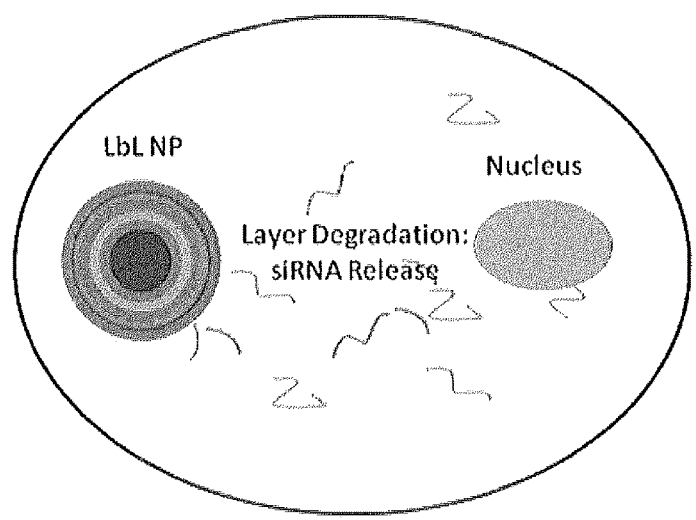
Figures 2, 3:
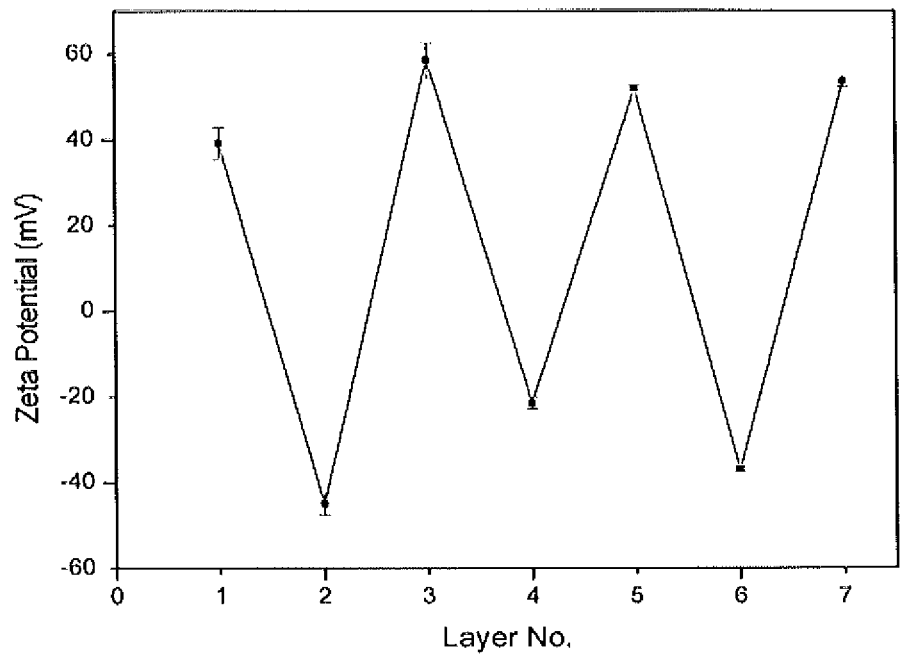
FIG. 2. The insertion of siGLO (siGLO Green Transfection Indicator, a fluorescent oligonucleotide duplex that localizes to the nucleus) within the multilayers of Layer-by-Layer (LbL) coated PEM nanoparticles. The siGLO coating onto PEM nanoparticles was determined by zeta potential: Shown are alternating zeta potentials of PEM nanoparticles resulting from alternating coating with positively charged poly-L-arginine and negatively charged dextran sulfate polyelectrolyte as well as siGLO layers. The negatively charged siRNA is loaded onto layers 4 and 6 resulting in significantly negative zeta potentials. Means and standard deviations of three independent measurements are shown.
FIG. 3. Table summarizing the sizes, dispersities and zeta potentials of multilayer nanoparticles with an increasing number of layers (HA=hydroxyapatite; ARG=poly-L-arginine, DXS=dextran sulphate, SPARC=SPARC siRNA)
Figure 4:
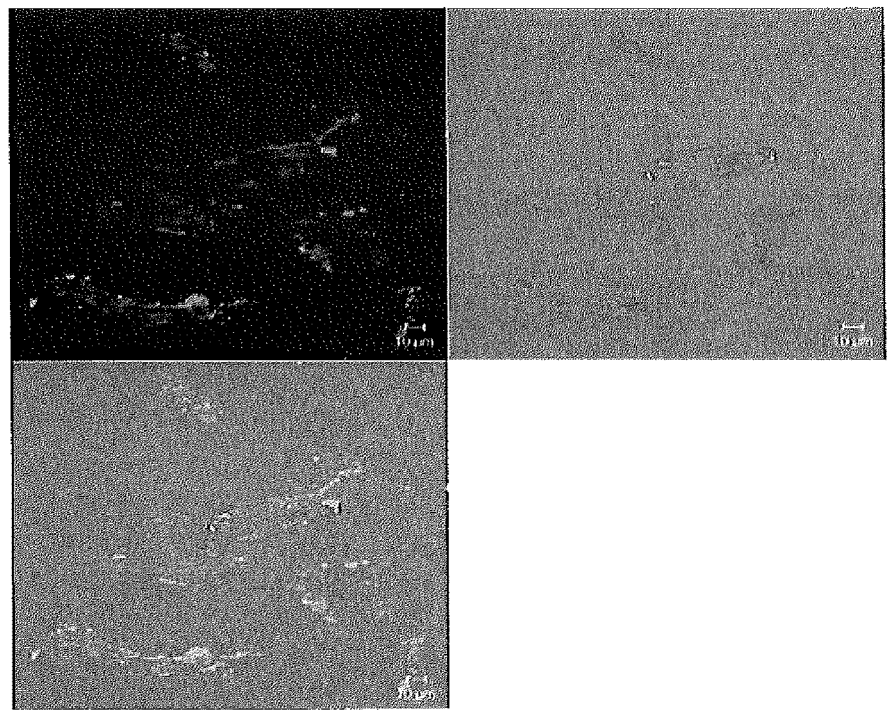
FIG. 4. The uptake of siGLO containing PEM nanoparticles by cells. Shown are confocal laser scanning microscopy images of FibroGRO cells 1 day after incubation with siGLO-loaded PEM nanoparticles. The dot-like green fluorescence inside the cell bodies demonstrates the uptake of siGLO-loaded PEM nanoparticles by FibroGRO which is especially illustrated by the transmission light and the overlay of both.
Figure 5:
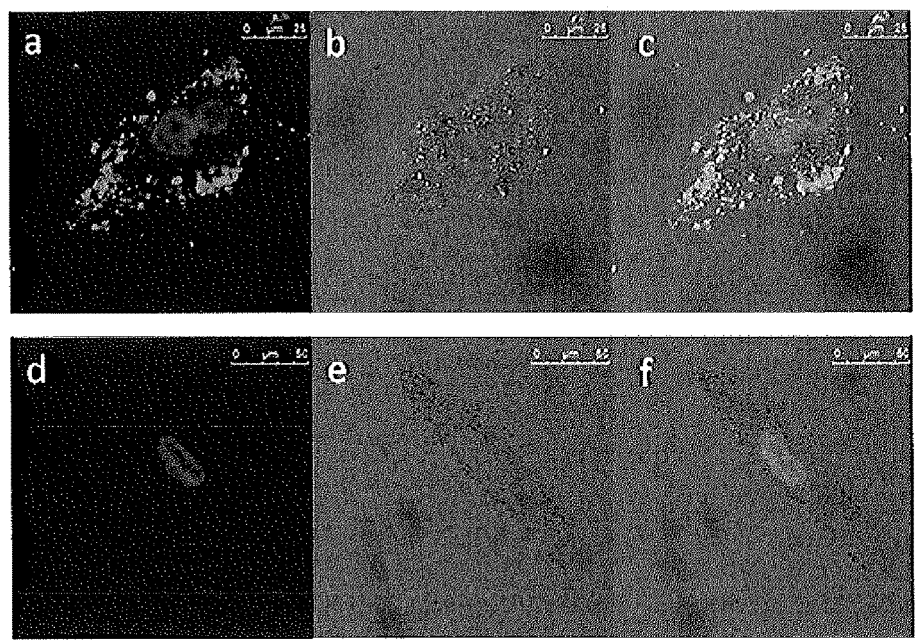
FIG. 5. The cellular interaction of siGLO containing LbL NPs. Shown are confocal laser scanning microscopy images of (a-c) FibroGRO cells one day after incubation with siGLO-loaded LbL nanoparticles. (a) The dot-like green fluorescence inside the cell bodies demonstrates the uptake of siGLO-loaded LbL nanoparticles by FibroGRO which is especially illustrated by (b) the transmission light and (c) the overlay of both. Unlabeled controls (FibroGRO cells incubated with LbL NPs containing unlabeled siRNA) are shown in traces (d-f). The transmission is demonstrated in trace (e) whereas the overlay can be seen in trace (f). Nuclei are stained by means of DAPI in order to clearly distinguish from the cytoplasm. Shown are representative confocal images of three independent measurements.
Figure 6:
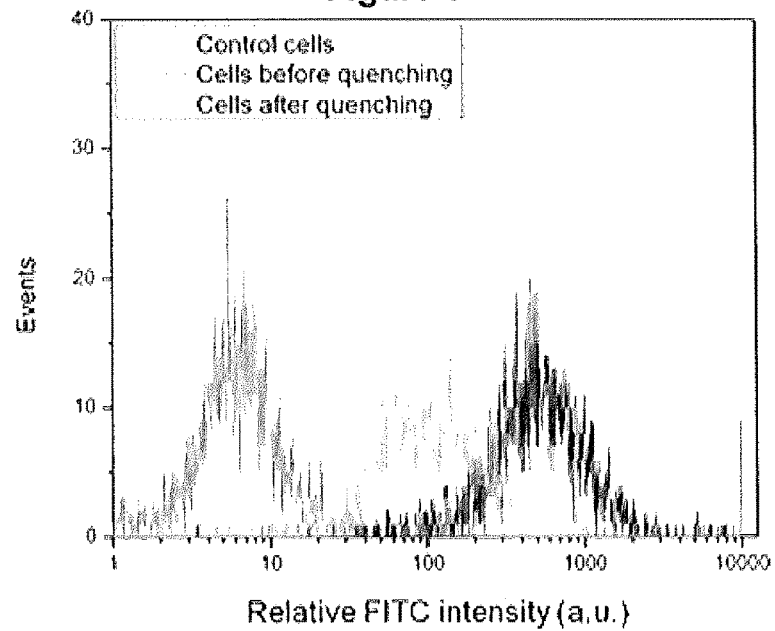
FIG. 6. Flow cytometric detection of cellular nanoparticle uptake. HA nanoparticles, coated with ARG, DXS and siGLO were coincubated with FibroGRO cells for one day. The histogram of siGLO-loaded LbL NPs treated FibroGRO cells before (black graph) and after (light grey graph) trypan blue quenching is shown. FibroGRO cells treated with LbL NPs containing unlabeled siRNA (grey graph) serve as control. Representative data of three independent measurements are shown.

The inventors have developed multilayer nanoparticles that possess significant advantages as RNA carriers. As highly customizable carrier systems, they have the potential to provide high uptake efficiency, as well as for localized RNA release as shown in FIG. 1. Polyelectrolytes of the particle surface can interact with several macromolecules of the cytoplasm, thus facilitating multilayer decomposition. The gradual degradation of the biopolymer layers occurring within cells allows release of the multilayer incorporated cargo.

Accordingly, a first aspect of the invention relates to, multilayered nanoparticles for delivery of RNA to a cell, the nanoparticles comprising: a core nanoparticle coated by alternating positively and negatively charged polymer layers, wherein the number of layers is 2 or more and wherein the at least one of the negatively charged polymer layers comprises or consist of RNA.

As used herein "multilayer nanoparticle" refers 2 or more layers coated on a nanoparticle core. As the layers are preferably coated using a layer-by layer process, the multilayer nanoparticles may also be referred to as layer by layer nanoparticles (LbL NPs). The first of the at least two layers that is coating the nanoparticle core directly, i.e. is in direct contact with the core surface, is referred to as the innermost layer. The top layer coating that forms the outer surface of the multilayer nanoparticle, i.e. the polymer layer farthest away from the core surface, is referred to as the outermost layer. It is understood that this outermost polymer layer may additionally be coated by a targeting compound, as detailed below.

It is generally possible to have 1, 2, 3, 4, 5, 6, 7, 8, 9, 10 or more layers between the inner most layer and the outer most layer. However, in various embodiments the multilayered nanoparticle comprises 3 to 10 layers.

Preferably the multilayer nanoparticle has a size from about 100 to about 5000 nm and is essentially spherical in form. The diameter of the multilayer nanoparticle as described herein can range from about 100 nm to about 500 nm; about 120 nm to about 450 nm; about 200 nm to about 300 nm; In some embodiments, the diameter of the diameter of the multilayer nanoparticle is in the range of about 200 nm to about 500 nm.

As used herein "RNA" refers to ribonucleic acid (RNA). RNA may be of biological or synthetic origin and may be single or double stranded. Such RNA can be messenger RNA (mRNA), small nuclear RNA (snRNA), ribozymes, or RNA used in RNA interference, such as microRNA or small interfering RNA (siRNA). In various embodiments the RNA is selected from the group consisting of ribozymes, RNAi and siRNA. In some embodiments described herein the RNA is siRNA.

As used herein, "siRNA" refers to small interfering RNA. siRNA is a short, typically 18-25 nt, double-stranded RNA molecule, with one of the strands (guide strand) being complementary to a target mRNA in cells, with the mRNA being transcribed from the gene that is being targeted for "silencing". One option for delivering siRNA involves the use of coated nanoparticles as described herein.

As used herein, "nanoparticle core" refers to any particle having a size from about 1 to about 250 nm. The diameter of the nanoparticle core as described herein can range in the size from about 1 nm to about 250 nm; about 1 nm to about 200 nm; about 1 nm to about 160 nm; about 1 nm to about 140 nm; about 1 nm to about 120 nm; about 1 nm to about 80 nm; about 1 nm to about 60 nm; about 1 nm to about 50 nm; about 5 nm to about 250 nm; about 8 nm to about 250 nm; about 10 nm to about 250 nm; about 20 nm to about 250 nm; about 30 nm to about 250 nm; about 40 nm to about 250 nm; about 85 nm to about 250 nm; about 100 nm to about 250 nm; or about 150 nm to about 250 nm. In some embodiments, the diameter of the diameter of the nanoparticle core is in the range of about 1 nm to about 100 nm.

In various embodiments, the nanoparticle core is essentially spherical.

In certain embodiments, the core may be negatively charged to facilitate the coating with a first positively charged polymer layer. In other embodiments, the core may be positively charged such that coating with a negatively charged first layer is facilitated.

In some embodiments the multilayer comprises at least 2 negatively charged polymer layers comprising or consisting of RNA. In this embodiment preferably the total number of layers is at least 5 layers and at least 2 of the negatively charged polymer layers comprise or consist of RNA. This has the advantage of providing sustained release of the RNA in a cell whereby the activity of the RNA can be measured at least two weeks after the multilayer nanoparticle has contact with the cell. Of course, the number of layers of the particle can be further increased to accommodate 3 or more RNA(-containing) layers.

In various embodiments the nanoparticle core is biocompatible or biodegradable.

The terms "bioabsorbable", "biodegradable" and "bioresorbable", as used interchangeably herein, refer to the ability of a material to degrade or breakdown over a period of time due to the chemical and/or biological action of the body and be safely excreted or removed from the body via the natural systems such as the excretory system. In the context of the present invention, the term "bioabsorbable" refers to one or more components that can be completely removed from a localized area by physiological metabolic processes such as resorption. For example, a biodegradable nanoparticle core may, when taken up by a cell, be broken down into smaller subunits by cellular machinery, such as lysosomes or by hydrolysis. Then the cells can either reuse or dispose of the remains without significant toxic effect on the cells. Examples of biodegradation processes include enzymatic and non-enzymatic hydrolysis, oxidation and reduction. Suitable conditions for non-enzymatic hydrolysis, for example, include exposure of biodegradable material to water at a temperature and a pH of a lysosome (i.e. the intracellular organelle). The degradation fragments typically induce no or little organ or cell overload or pathological processes caused by such overload or other adverse effects in vivo.

Various examples of biodegradable materials are known in the art, any of which are generally suitable for use in and are not toxic to organisms may be used in the present invention. Examples of materials that are considered to be biodegradable and suitable for use according to the instant invention include, without limitation, aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, polycarbonates, naturally-occurring biodegradable polymers such as chitosan, collagen, starch, and blends thereof. Examples of polyorthoesters include polylactide, polyglycolide, polycaprolactone, polylactic acid, biodegradable polyamide, biodegradable aliphatic polyester, and/or copolymers thereof, polylactic acids (PLA), polycaprolactone (PCL), and polylactic-co-glycolic acid (PLGA).

As used herein "biocompatible" refers to a synthetic or natural material that does not interfere with biological processes and may be considered as a biologically or chemically inert material. Various examples of biocompatible materials are known in the art, any of which that are generally suitable for use in and are not toxic to organisms may be used in the present invention. Examples of materials that are considered to be biocompatible and suitable for use according to the present invention include, without limitation, hydroxyapatite, silica, calcium carbonate, gold, polystyrene latex.

In various embodiments the nanoparticle core comprises or consists of a material selected from the group consisting of hydroxyapatite, silica, poly(lactide-co-glycolide) (PLGA), poly(lactic acid) (PLA), calcium carbonate, gold, polystyrene latex, preferably hydroxyapatite.

The use of biocompatible and biodegradable nanoparticles, such as hydroxyapatite, is much less cytotoxic than any previous candidates described to have delivered RNA.

In various other embodiments, the nanoparticle core comprises a liposome, preferably a nanoliposome.

As used herein the term "liposome" refers to any lipid bilayer vesicle structure comprised of lipids and/or lipid derivatives and/or lipid-like molecules, including phospholipids.

In various embodiments the liposome may be loaded with RNA, such that the RNA is encapsulated within the liposome, prior to being coated with the two or more alternating positively and negatively charged polymer layers containing at least one RNA layer. The outermost layer may be constructed from cell-targeting peptides as described below.

As used herein the term "nanoliposome" refers to nanoscale lipid vesicles. The underlying mechanism for the formation of liposomes and nanoliposomes is basically the hydrophilic-hydrophobic interaction between amphiphilic lipids and water molecules. Vesicles prepared in nanometric size ranges serve as the nanoparticle core that is then subsequently coated with alternating positively and negatively charged polymer layers containing at least one RNA layer as described herein. Targeted therapy can also be achieved efficiently via multilayered nanoparticle using liposomes or nanoliposomes as the nanoparticle core and employing passive or active targeting mechanisms such as cell-targeting peptides as described herein.

The term "layer", as used herein, refers to a coating film that covers at least part of the nanoparticle core and/or the layer below. The layer is preferably continuous and covers essentially the complete surface of the core or the layer directly beneath. The layer thickness can be controlled by manufacturing conditions, but typically ranges from 1 to 110 nm.

In various embodiments of the multilayered particles described above, the outermost layer is a positively charged polymer. Compared to other delivery methods the multilayered nanoparticles approach allows for greater protection of the RNA molecule while it is being transported into the cytoplasm, and perhaps also during the period it spends in the cytoplasm, because the outermost layer is not RNA, but a positively-charged polyelectrolyte.

In various embodiments the innermost layer is a positively charged polymer.

In various embodiments the RNA layer is sandwiched between two positively charged polymer layers. This has the advantage of protecting the RNA, because the outermost layer is not RNA and it allows for a slower release of the RNA into the cell.

In various embodiments the positively charged polymer is a polycation

In various embodiments the negatively charged polymer is a polyanion.

As used herein the term "polycation" or "polyanion" refer to polyelectrolytes or polymers whose repeating units bear an electrically charged or potentially electrically charged group. In the latter case, these groups dissociate in aqueous solutions (water), making the polymers charged. Polycations are polymers with a positive net charge. Polyanions are polymers with a negative net charge.

By coating a core nanoparticle with alternating positively and negatively charged polymer layers the incorporated RNA layer is protected until it is released within the cell cytoplasm where it is able to effectively perform its function. The multilayers provide both protection of the RNA and gradual release.

In various embodiments the positively charged polymer comprises or consists of poly (L-arginine).

In various embodiments the negatively charged polymer comprises or consists of dextran sulphate.

In various embodiments the multilayered nanoparticle further comprises a targeting peptide or protein as the outermost layer.

As used herein the term "targeting peptide" or "protein" refers to proteins or peptides that directs the transport of the multilayer nanoparticles into the cell of interest. It may also be referred to as a signal peptide. They may include antibodies or a short peptide (3-70 amino acids long) that recognizes specific cell receptors or channels. In various embodiments the targeting peptide or protein is selected from TAT peptide, endocytosis mediated amphiphilic peptide, and folate receptor targeting moieties.

The multi-layer approach also easily allows for using targeting peptides as the outermost layer, which will then enable target-specific delivery of the particles and of siRNA. Such targeting peptides include, TAT peptides, endocytosis mediated amphiphilic peptide such as, Endoporter® peptides and Folate receptor-targeting moieties.

In various embodiments the RNA is siRNA and targets a Secreted Protein, Acidic and Rich in Cysteine (SPARC) gene.

In various embodiments the siRNA has a nucleotide sense sequence set forth in SEQ ID NO:1 (AACAAGACCUUC-GACUCUUUC) and a nucleotide antisense sequence set forth in SEQ ID NO:2 (GGAAGAGUCGAAGGUCUU-GUU).

Another aspect of the invention relates to a method for manufacturing the multilayered nanoparticle as described herein, comprising the steps of: a) Providing a nanoparticle core; b) Contacting the nanoparticle core with a positively charged or negatively charged polymer to form a first polymer layer on the nanoparticle core; c) Contacting the coated nanoparticle of step b) with a polymer charged opposite to that used in step b) to form a second polymer layer on the nanoparticle; d) Optionally repeating steps b) and c), wherein at least one of the negatively charged polymer layers comprises or consist of RNA.

Another aspect of the invention relates to a method for the delivery of RNA (siRNA) to a cell or organism comprising: contacting said cell or organism with an effective amount of the multilayered nanoparticle as described herein.

As used herein the RNA may be delivered to a cultured cell in vitro or it may be delivered to the cell in vivo. The cell may be any cell including prokaryotic cells or eukaryotic cells of any organisms in which RNA is to be delivered.

In various embodiments, the organism may refer to a bacteria, a fungus, a plant or an animal, preferably the organism is a mammal such as a rat, mouse, horse, or human.

Another aspect of the invention relates to a method for the treatment of an RNA-treatable disease or disorder in a subject, comprising administering an effective amount of the multilayered nanoparticle as described herein to the subject.

The term "RNA-treatable disease or disorder" relates to any condition that is amenable to treatment with RNA. Exemplary diseases include, without limitation, hyperproliferative diseases, including cancer, but also hypertension, diabetes, liver cirrhosis and inflammatory diseases.

As used herein the term "subject" refers to a bacteria, a fungus, a plant or an animal, preferably the organism is a mammal such as a rat, a mouse, a horse, or a human.

In various embodiments the RNA is siRNA that inhibits Secreted Protein, Acidic and Rich in Cysteine (SPARC) expression to reduce scarring in the subject.

In various embodiments the effective amount of the multilayered nanoparticle is administered to a conjunctiva after surgery, wherein preferably the RNA is siRNA that inhibits Secreted Protein, Acidic and Rich in Cysteine (SPARC) expression.

Another aspect of the invention relates to a use of the multilayered nanoparticle as described herein for the delivery of an RNA to a cell or organism.

Another aspect of the invention relates to a multilayered nanoparticle as described herein for use in the treatment of RNA-treatable diseases or disorders.

In various embodiments, the RNA is siRNA that inhibits Secreted Protein, Acidic and Rich in Cysteine (SPARC) expression to reduce scarring in a mammal such as a rat, a mouse, a horse, or a human.

In various embodiments a biocompatible hydroxyapatite nanoparticle core is coated with poly-arginine and dextran sulphate (DXS) layers as well as layers incorporating or consisting of SPARC-siRNA. It could be demonstrated that such SPARC siRNA-loaded multilayer nanoparticles were successfully taken up by mouse fibroblasts to deliver the siRNA. This demonstrates successful knock-down of SPARC-protein in these cells. The initial cellular binding, which is crucial for cellular uptake, is facilitated by the positively charged surface layer (ARG), leading to uptake by endocytosis, as indicated by co-localization of nanoparticles with endosomes. This is followed by endosomal escape of (mostly) intact nanoparticles with the charged outer layer facilitating pore formation within the endosomes. Up to 60% sparc-protein knock down was achieved with a single multilayer nanoparticles treatment. Relative SPARC and RPL13 mRNA levels significantly were reduced to 0.4±0.04 folds, demonstrating that efficient SPARC gene silencing can be achieved by the multilayer nanoparticles approach. In addition there was no observed cytotoxicity associated with multilayer nanoparticles treatment in fibroblasts supporting the safety of multilayer nanoparticles as a potential non-viral vector for RNA delivery such as siRNA. In conclusion, these findings support the promising development of layer-by-layer nanoparticles as a non viral therapeutic approach to knock down mRNA.

It has thus been demonstrated that SPARC-siRNA loaded multilayer nanoparticles composed of ARG as polycation and DXS as polyanion could effectively deliver siRNA into fibroblast cells with much lower cytotoxicity. Moreover, SPARC-siRNA delivered by multilayer nanoparticles could specifically reduce target protein expression levels in fibroblast cells. These multilayer nanoparticles with HA (hydroxyapatite) as core have several advantages over chemical conjugates of siRNA based delivery vectors. First, the formulation steps are very simple, reducing the time for preparation of siRNA delivery systems. Toxicity of the multilayer nanoparticles RNA delivery vehicles appeared to be low, as indicated by cytotoxicity studies.

This finding represents an important advantage for multilayer nanoparticles systems, because a limiting factor for gene delivery using other non-viral particles, has been toxicity.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples.

EXAMPLES

Manufacturing an siRNA Multilayered Nanoparticle

Starting with nanoparticle core made of any material for example, hydroxyl apatite (HA), the core is coated with alternating positive and negative layers. In a typical scheme, 100 nm HA particles are first coated with a cationic polymer such as L-arginine (+ve charge), followed by dextran sulfate (−ve charge); subsequent −ve layers may be made of the siRNA molecule (which is negatively charged). A 6-layer system may be made this way as depicted in FIG. 1.

One siRNA molecule used was called siGLO as it has a fluorescent tag. Multilayer or Layer-by-Layer (LbL) nanoparticles (NPs) were fabricated using commercially available HA NPs as the core coated with the oppositely charged biopolymer layers ARG, DXS with SPARC siRNA in the bilayers. The SPARC-siRNA coatings in the bilayers and the concentration of the polyelectrolytes were optimised to build the multilayered NPs, appreciable siRNA loading and to prevent agglomeration. Since siRNA coating into the NP multilayer is only meaningful if layer delamination with a subsequent siRNA release into the cytoplasm takes place, the defoliation was studied by means of siRNA reporter molecules incorporated into LbL multilayer. To evaluate cellular uptake of LbL NPs, siGLO-siRNA green transfection indicator was coated in the bilayers of LbL NPs as a negatively charged layer; the particle size of siGLO-LbL NPs is 485 nm with zeta potential of +43 mV. The actual amount of siGLO coated on bilayers is 0.4 pmole/μg of LbL nanoparticles with coating efficiency of 98%±0.2. The amount reported here is deemed sufficient for gene silencing.

Materials

Hydroxyapatite (HA) nanoparticles (<200 nm), poly-L-arginine hydrochloride (ARG) (MW>70,000) and Dextran sulfate sodium salt (DXS) (MW>360000) were procured from Sigma (Singapore) and MP Biomedicals LLC (Singapore). siGLO green transfection indicator was obtained from Dharmacon, Thermo Scientific (Singapore). Lysotracker Red DND-99 and Opti-MeM reduced serum medium was from Invitrogen (Singapore). FibroGRO human foreskin fibroblasts were from Millipore (Singapore). Dulbecco's modified Eagle's medium (DMEM with high glucose and with L-glutamine), Dulbecco's PBS without calcium and magnesium, trypsin-EDTA, penicillin-streptomycin and fetal bovine serum (FBS) were from PAA laboratories (Singapore). Trypan blue stock solution (0.4%) was purchased from Sigma-Aldrich (Singapore). SPARC-siRNA Mw-13369 g/mole and scrambled were procured from Bio-Rev, South Korea.

```
SPARC-siRNA:
sense-
                                     (SEQ ID NO: 1)
AACAAGACCUUCGACUCUUUC antisense-
                                     (SEQ ID NO: 2)
GGAAGAGUCGAAGGUCUUGUU scrambled siRNA
sense-
                                     (SEQ ID NO: 3)
GCUCACAGCUCAAUCCUAAUC antisense-
                                     (SEQ ID NO: 4)
GAUUAGGAUUGAGCUGUGAGC
```

Process

Hydroxyapatite nanoparticles (NPs) were suspended in 0.2 μm filtered purified water (Millipore), vortexed for five minutes and collected by centrifugation (ST16R, Sorvall) at 12000 rpm for one min, the procedure is repeated to wash the HA nanoparticles. The nanoparticles suspension is added to equal amount of 0.5 mg/mL poly(L-arginine, ARG) followed by vortex and sonication for ten minutes and the ARG coated NPs were collected and washed using sodium chloride. The ARG coated NPs were resuspended in sodium chloride and added to 0.5 mg/mL dextrin sulphate (DXS) as anionic layer and in case of SPARC-siRNA, 4 μL of 20 nM solution is used in the siRNA coating with incubation time of thirty min. Final layer of LbL coating was achieved by adding siRNA coated LbL NPs to ARG followed by incubation for 10 minutes. Samples for size and zeta potential measurements were collected for each layer, in case of siRNA layer the measurements were carried out in nanodrop (V3.7, Thermoscientific) at 230 nm to estimate the siRNA coating on the LbL NPs. We have incorporated siGLO, reporter-siRNA, SPARC-siRNA in LbL NPs separately and the LbL NPs were designated as follows: HA|ARG|DXS|ARG|siRNA|ARG.

One nanoparicle was made whereby the only negatively charged polymer was RNA. Hydroxyapatite nanoparticles (NPs) were suspended in 0.2 μm filtered purified water (Millipore), vortexed for five minutes and collected by centrifugation (ST16R, Sorvall) at 12000 rpm for one min, the procedure is repeated to wash the HA nanoparticles. The nanoparticles suspension is added to an amount of 0.5 mg/mL poly(L-arginine, ARG) followed by vortex and sonication for ten minutes and the ARG coated NPs were collected and washed using sodium chloride. The ARG coated NPs were resuspended in sodium chloride and added to 12 μL of 1200 pmole solution is used in the SPARC siRNA coating with incubation time of thirty min. Final layer of LbL coating was achieved by adding siRNA coated LbL NPs to ARG followed by incubation for 10 minutes. Resulting in a multilayer nanoparticle structure of [HA|ARG|siRNA|ARG]

Figure 7:
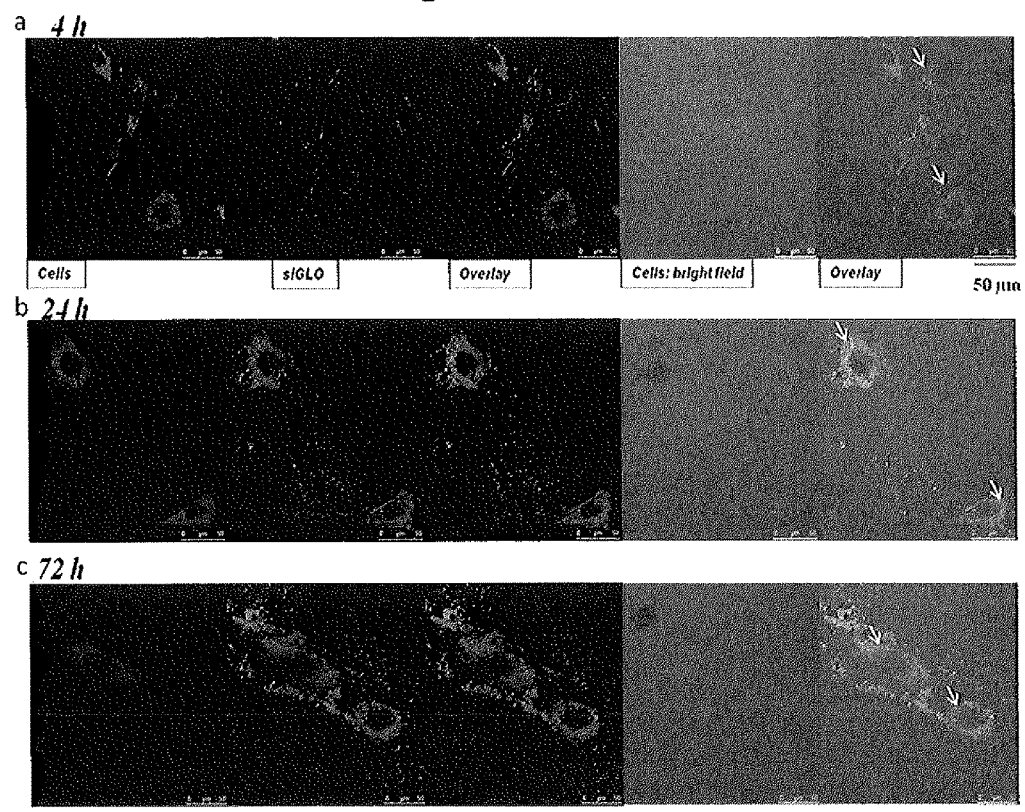
FIG. 7. The localization of siGLO-loaded LbL NPs within FibroGRO cells. Shown are CLSM investigations of the nanoparticle uptake by FibroGRO cells and a concomitant lysosomal stain. The staining with lysotracker red was performed at different time points; (a) 4 h, (b) 24 h and (c) 72 h. The arrows in FIGS. 3b and 3c point to co-localized regions of NPs and endosomes (orange colour). At 72 hours, the diffuse green regions in FIG. 3c are due to the coalescence of siRNA molecules that have been 'released' from the NPs. Scale bar represents 50 μm. Shown are representative confocal images of three independent measurements.

Another nanoparticle was made whereby the only negatively charged polymer was RNA and there were 2 layers of RNA. Hydroxyapatite nanoparticles (NPs) were suspended in 0.2 μm filtered purified water (Millipore), vortexed for five minutes and collected by centrifugation (ST16R, Sorvall) at 12000 rpm for one min, the procedure is repeated to wash the HA nanoparticles. The nanoparticles suspension is added to an amount of 0.5 mg/mL poly(L-arginine, ARG) followed by vortex and sonication for ten minutes and the ARG coated NPs were collected and washed using sodium chloride. The ARG coated NPs were resuspended in sodium chloride and added to 12 μL of 1200 pmole solution is used in the SPARC siRNA coating with incubation time of thirty min. Final layer of LbL coating was achieved by adding siRNA coated LbL NPs to ARG followed by incubation for 10 minutes. The ARG coating and the SPARC siRNA coating were each repeated in the same way another time resulting in a multilayer nanoparticle structure of [HA|ARG|siRNA|ARG|siRNA|ARG]

Characterization of the Multilayered Nanoparticles

The layering can be verified using zeta potential measurements of the particle following deposition of each layer, as shown in FIG. 2.

The influence of LbL nanoparticles on the size and surface charge with SPARC-siRNA loaded LbL NPs was also investigated and results are depicted in FIG. 3. The SPARC-siRNA coated LbL NPs yields a size of 350 nm with zeta potential of +43 mV. The coating efficiency of SPARC-siRNA is 97% with 0.4 pmole SPARC/μg of LbL nanoparticles. For gene silencing studies, this concentration (0.4 pmole/μg of LbL nanoparticles) was used to treat the FibroGRO cells.

Electrophoretic Mobility

The electrophoretic mobility of the LbL NPs after coating of each layer was measured in 0.2 μm filtered 0.1 M Nacl at room temperature using a Malvern Zetasizer 2000 (Malvern Instruments). The zeta-potential (ζ-potential) was calculated from the electrophoretic mobility (μ) using the Smoluchowski function $\zeta=\mu\eta/\varepsilon$ where η and ε are the viscosity and permittivity of the solvent, respectively.

Delivery of RNA to a Cell

To determine if the multilayered nanoparticle can be delivered to a cell the siGLO particles manufactured as described above were incubated with cells to assess the entry of the particle into the cytoplasm. This is done by using a tagged siRNA particle, called "siGLO". If the particle with the siGLO coating enters the cell, it is made visible by confocal microscopy using the desired wavelength laser as depicted in FIG. 4.

The LbL system based on hydroxyapatite (HA) provides efficient gene knockdown in fibroblasts. The knockdown efficiency was tested with a layer by layer construction using poly-L-arginine (ARG), dextran sulfate (DXS), optimized for cellular penetration and defoliation.

This carrier incorporates the SPARC-siRNA for the intracellular transport and for targeting the SPARC-mRNA in fibroblasts (FibroGRO). In order to study cellular binding, uptake, intracellular processing of SPARC-siRNA coated onto LbL NPs, siGLO-Green transfection indicator (siGLO) was used as a multilayer constituent in LbL NPs. Nanoparticle uptake and cellular transfection were investigated in FibroGRO cells by means of confocal microscopy and flow cytometry. The targeted protein expression levels in FibroGRO™ cells are evaluated by ChemiDOC® western blot technique, while the mRNA levels (post LbL treatment) was quantified by using RT-PCR.

Multilayered Nanoparticle with siGLO

Cellular binding is facilitated by electrostatic interaction between positively charged LbL NPs and the cell membrane. Consequently, the charge of the outermost LbL NPs layer plays a key role in the first step of LbL NPs/cell interaction. Therefore, cellular uptake by FibroGRO was studied with LbL NPs containing ARG as outermost multilayer component. Apart from charge, size is an important parameter influencing the cellular uptake rate. The multilayer nanoparticles are easily taken up by cells compared to microparticles. LbL NPs binding and uptake were analyzed both qualitatively using CLSM and quantitatively by using flow cytometry (FCM) (2.5 ng LbL NPs/cell). FIG. 5 shows typical CLSM images of a considerable number of LbL NPs inside and attached to FibroGRO (a-c) cells after one day of incubation. Controls containing LbL NPs with unlabeled siRNA are shown in traces d-f. According to the transmission (b, e) and overlay (c, f) pictures, the fluorescent particles were only present at cell membranes and in the cytoplasm, but not inside the nuclei. Nuclei stain by means of DAPI supports this finding that no particles can be found in the nuclei. This indicates that FibroGRO cells were able to internalise the siGLO-loaded LbL nanoparticles, however the particles were too large for nuclear entry. This result corroborates with the findings of Zhou et. al. (Macromol. Biosci. 2009, 9, 326.) that 400 nm PLGA nanoparticles with chitosan/alginate multilayer are incorporated into hepatocytes, but no nuclei localization could be found in the confocal images.

The LbL nanoparticles uptake in FibroGRO cells was studied by flow cytometer measurements involving trypan blue quenching to avoid surface bond nanoparticles on the cells. (FIG. 6). The nanoparticles internalized in the cells are protected from trypan blue quenching as living cells do not allow trypan blue penetration. However, particles bound towards the outer surface of the cell membrane will be exposed to trypan blue and subsequently be quenched.

The comparison of the fluorescence intensities of FibroGRO cells treated with control LbL NPs containing unlabeled siRNA with Gmean-8±0.1 and siGLO loaded-LbL NPs after quenching with Gmean-100±0.7 clearly indicates cellular uptake of LbL nanoparticles. The fluorescence intensity shift after treating LbL NPs to FibroGRO cells before and after quenching indicates a strong LbL NPs interaction with FibroGRO cells as a cellular uptake process. Trypan blue addition to FibroGRO cells treated with siGLO containing LbL NPs resulted in a rather marginal fluorescence intensity shift. Since the cellular fluorescence intensity after trypan blue quenching is higher than the fluorescence intensity of the control cell group, this indicates successful internalization of the LbL NPs by the FibroGRO cells.

In order to obtain information on internalization and intracellular localization of the RNA loaded LbL NPs, staining with the Lysotracker was performed during LbL NPs uptake. As gene silencing takes place at the mRNA stage in the cytosol, the fate of the NPs inside the cells and the intracellular localization must ensure the availability of siRNA in this compartment. Escape from the endosomes is important for the effective delivery of siRNA into the cytosol.

FIG. 7 depicts live cell confocal images captured at various particle incubation times: at four hours post LbL incubation (FIG. 7a) we see cells surrounded by the LbL NPs but also some spotty green fluorescence within the cells, indicating the presence of siGLO within the NPs. The spotty nature of the fluoroscence is attributed to siGLO still incorporated within NPs (possibly aggregated). As the incubation time increased to 24 h a colocalization of the green-siGLO fluorescence and the red lysotracker was visible (orange or yellow colour, overlaid in FIG. 7b) indicating LbL particle localization inside endosomes. At 72 hours, FIG. 7c shows spotty fluorescent (green) regions as well as diffuse regions within the cells. This is attributed to successful escape of NPs incorporating siGLO from the endosomes with some concurrent or sequential release of free siGLO molecules that then coalesce to form diffuse green regions.

Figure 8:
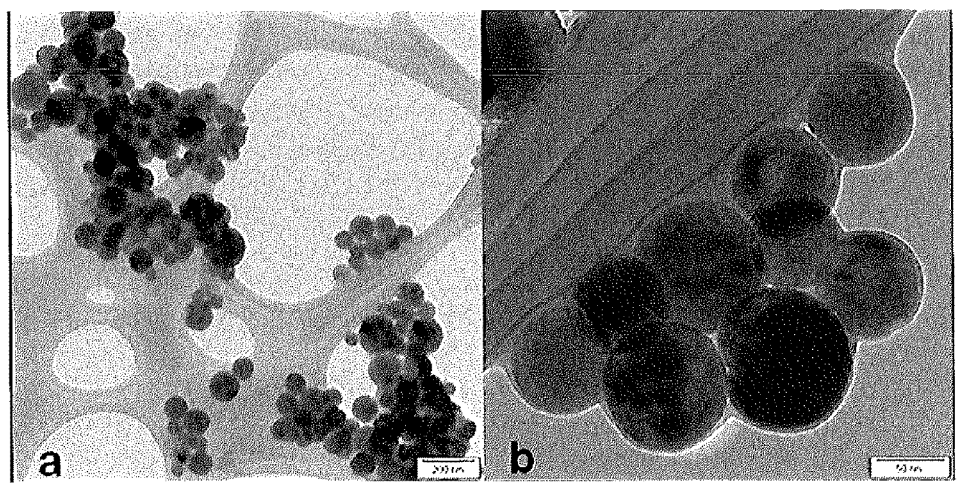
FIG. 8. TEM images of SPARC-siRNA coated five layer LbL nanoparticles; scale bar (a) 200 nm; (b) 50 nm.

The release of siGLO associated with LbL NPs is inferred from fluorescence extension and coalescence of the spots and subsequent diffuse distribution of fluorescence throughout the cells. No siRNA-associated fluorescence was observed for untreated cells (blanks), and the co-localization of green-siGLO and endosomes followed by release of siGLO indicates LbL NPs were successfully taken up into the FibroGRO cells and that the siGLO release is gradual. In addition to the average LbL average particle size of 200 nm as determined by transmission electron microscopy (FIGS. 8a and 8b), the spherical shape and smooth morphology of siRNA coated LbL NPs also probably facilitate the effective cellular uptake. The FibroGRO cells uptake the poly(L-arginine) coated LbL NPs by endocytosis, as observed by endosomal colocalization[39] and further the siGLO-LbL NPs escape from endosomes by pore formation in the endosomal lipid bilayers. In the case of non-viral vectors such as positively charged NPs and surface modified PLGA NPs the major mechanism for cellular uptake is by endocytosis.

Endosomal acidification begins almost immediately upon the nanoparticle's scission from the plasma membrane, as its lumen no longer communicates with the surrounding intracellular media. The ARG peptide (with a pKa of ~11.5) is expected to be protonated at pH's much lower than 11, and so when they enter endosomes, are already fully positively charged (no proton sponge effect), Subsequently, the positively charged LbL NPs interact with phospholipid membranes to form pores large enough for the NPs to squeeze through. This escape is confirmed by the spotty green regions (which are not single particles, but could be aggregates). Subsequently, the layers defoliate to release siGLO molecules in the cytosol, and these molecules will coalesce to form diffuse green regions that grow over time of incubation. Herce et al. (Phys Rev Lett, 2004, 92, 19), and Huang et al. (Biophy J. 2009, 97, 1917) have reported that the binding of cationic peptides to the lipid bilayers leads to internal stress that can be sufficiently strong to create pores in the endosomal lipid membranes.

Cell Culture and Cellular Uptake of LbL NPs

FibroGRO cells derived from human foreskin were cultured in DMEM (10% FBS, penicillin/streptomycin) and incubated at 37° C., 5% $CO_2$. Cells were detached using trypsin-EDTA and passaged at ratios of 1:2 to 1:4.

$4 \times 10^3$ cells were seeded in eight well glass-bottom chamber slide (Nalgene Nunc International, Napperville, Ill., USA; size of one well: 0.7 cm×0.7 cm, in DMEM/10% FBS) overnight. The medium was changed to Opti-Mem before the addition of 10 μg of siGLO-loaded LbL NPs. Further post-incubation for 4 hrs, CLSM measurements were done by replacing medium with PBS. DAPI stain for cell nucleus counter stain was performed by adding 300 μL of 300 nM DAPI delectate to the cells for 5 min and rinsed with PBS. For tracking of acidic organelles within the cells, lysotracker red was added according to manufacturer's instructions. Confocal micrographs were captured using a confocal laser scanning microscope (CLSM), Zeiss LSM 510.

For flow cytometric analysis of cell-particle interaction, $2 \times 10^5$ FibroGRO cells per well were seeded in 6 well plates and cultured overnight. The medium was changed to opti-mem before addition of siGLO-loaded LbL NPs. Following 4 hours incubation, the cells were detached by incubation in trypsin-EDTA for 5 mins at 37° C. and mixed gently to achieve single cells before addition of twice the volume of complete medium. Complete removal of the medium was achieved by centrifugation at 300 rcf and subsequent washes with PBS. The cells were re-suspended in PBS and constantly stored on ice and in the dark until flow cytometry measurement. For quenching 10 μL of 0.4% trypan blue was added to the cells to remove membrane-bound LbL NPs. Flow cytometry of the cells was executed immediately and each experiment was repeated three times and one representative data is presented.

Flow Cytometry (FCM)

The fluorescence intensities of the labeled particles as well as cells incubation with the particles were investigated by FCM (FACS Calibur, Becton Dickinson, USA). siGLO Green was detected in the FL-1 channel (band pass: 530±15 nm) after a laser excitation at 488 nm. The $10^4$ events were detected in the relevant regions for carrier/cell interaction and analyzed using the WinMDI2.9 software.

Confocal Laser Scanning Microscopy (CLSM)

The visualization of NP/cell interaction and uptake was carried out by means of CLSM (Zeiss, LSM 510 Meta, Jena, Germany). To detect siGLO Green fluorescence intensities an Ar/Kr laser (excitation wavelength: 488 nm) was used, while red fluorescence (Lysotracker Red) was detected with a He/Ne laser (excitation wavelength: 543 nm). siGLO and Lysotracker Red emissions were detected with band pass filters (505-530 nm and 560-615 nm).

Multilayered Nanoparticle with SPARC-siRNA

A multilayered nanoparticle containing SPARC-siRNA in the bilayers of layer-by-layer (LbL) nanoparticles (NPs) with poly(L-arginine) (ARG) and dextran (DXS) as polyelectrolytes was delivered to a fibroblast cell culture. Cellular binding and uptake of LbL NPs as well as siRNA delivery were studied in FibroGRO™ cells. siGLO-siRNA and SPARC-siRNA were efficiently coated onto hydroxyapatite nanoparticles. The multilayered NPs were characterized with regard to particle size, zeta potential and surface morphology using dynamic light scattering and transmission electron microscopy. The SPARC-gene silencing and mRNA levels were analyzed using ChemiDOC® western blot technique and RT-PCR. The multilayer SPARC-siRNA incorporated nanoparticles are about 200 nm in diameter and are efficiently internalized into FibroGRO™ cells. Their intracellular fate was also followed by tagging with suitable reporter siRNA as well as with lysotracker dye; confocal microscopy clearly indicates endosomal escape of the particles. Significant (60%) SPARC-gene knock down was achieved by using 0.4 pmole siRNA/μg of LbL NPs in FibroGRO™ cells and the relative expression of SPARC mRNA reduced significantly (60%) against untreated cells. The cytotoxicity as evaluated by xCelligence real-time cell proliferation and MTT cell assay, indicated that the SPARC-siRNA-loaded LbL NPs are non-toxic. In conclusion, the LbL NP system described provides a promising, safe and efficient delivery platform as a non-viral vector for siRNA delivery that uses biopolymers to enhance the gene knock down efficiency for the development of siRNA therapeutics.

Figure 9:
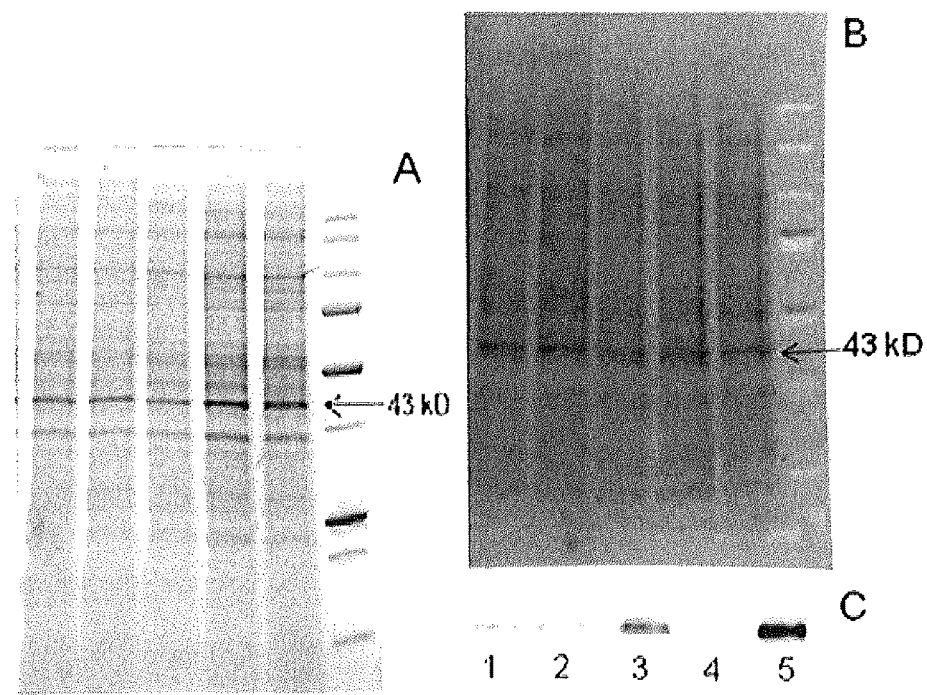
FIG. 9. Protein separation and antibody treatment using Biorad Chemidoc System: (A) Protein separation in stain free gels. (B) Protein transfer to PVDF membrane using Transblot® system. (C) The bands corresponding to SPARC (43 kDa) after substrate treatment viewed in Chemidoc imager with following sample sequence; (1) LbL NPs with SPARC-siRNA layer, (2) LbL NPs with SPARC-siRNA layer, (3) Blank cells, (4) Lipofectamine with SPARC-siRNA, (5) Lipofectamine with scrambled-siRNA.

Targeted protein levels were evaluation by a stain-free technology. FIG. 9 depicts the protein separation from all the lysed protein samples loaded in to the stain free gels, the bands corresponding to SPARC protein (43 kDa) in gel as well as in membranes clearly suggest the protein separation and transfer to the membrane by stain free (SF) technique. The bands corresponding to SPARC (43 kDa) after substrate treatment indicate the reduction in protein expression levels with LbL NPs containing SPARC-siRNA and lipofectamine with SPARC-siRNA but in case of blank cells and lipofectamine-scramble siRNA there was no decline in the band intensity indicating no reduction in the protein expression levels.

Figure 10:
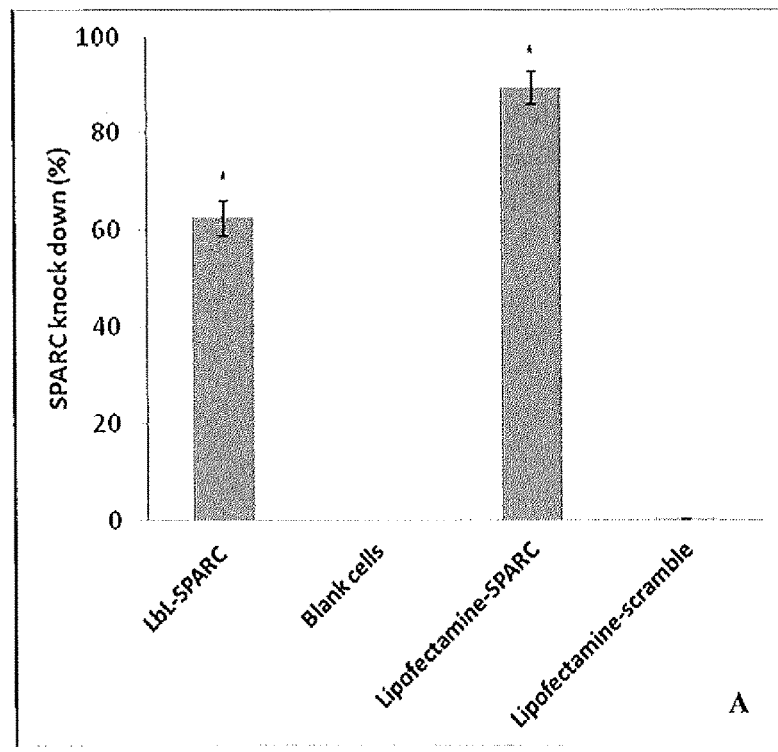
FIG. 10. Percentage Knock down efficiency of SPARC-siRNA loaded LbL nanoparticles in fibroGRO cells, A 96 h post nanoparticles treatment. LbL nanoparticles were composed of one layer of SPARC-siRNA, Blank cells and Lipofectamine (LF) with SPARC-siRNA, LF with scrambled-siRNA. B 2 days, C 7 days and D 14 days. *$p<0.001$. Results were obtained from three independent experiments.
Figure 10:
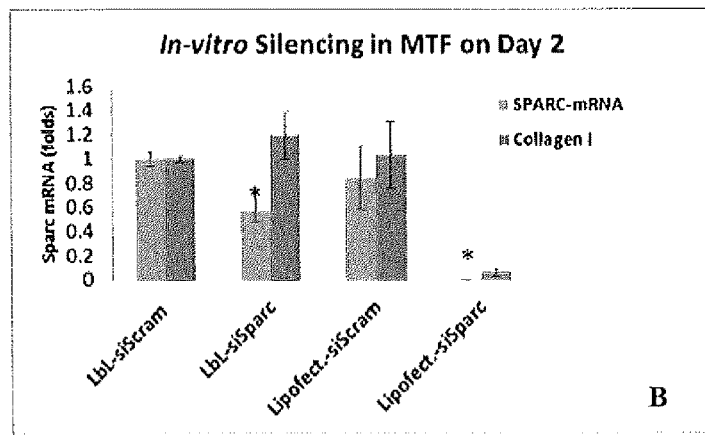
Figure 10:
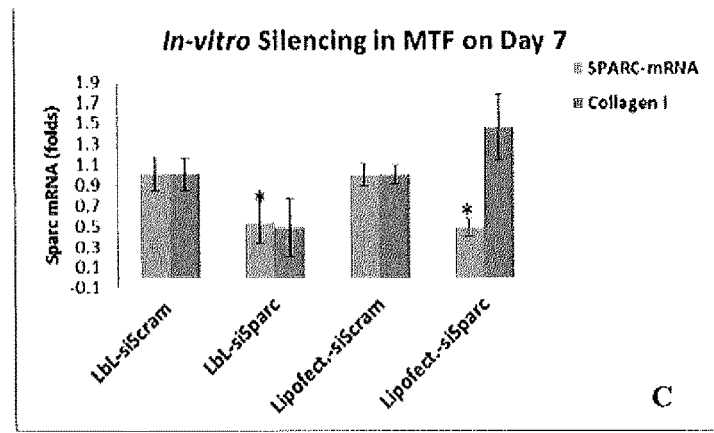
Figure 10:
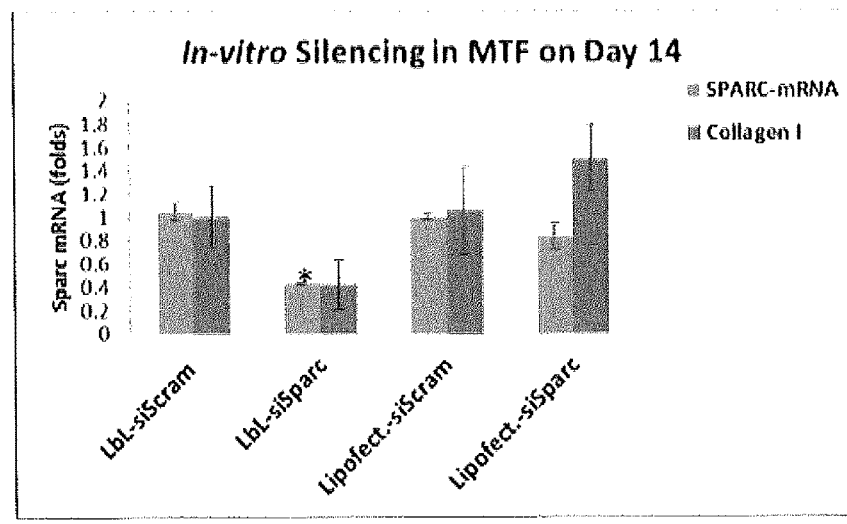
Figure 11:
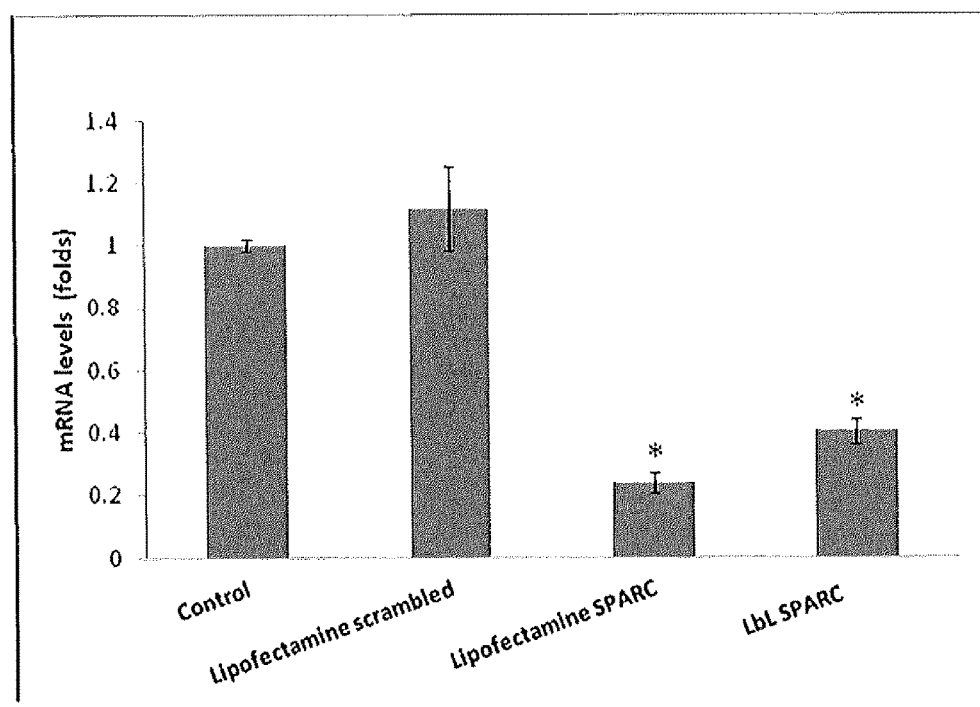
FIG. 11. Relative mRNA levels of SPARC and RPL13 showing efficient gene silencing using SPARC-siRNA loaded LbL NPs in FibroGRO cells. Values are shown as relative to control on 96 h post LbL treatment with LbL-SPARC siRNA, Lipofectamine-SPARC siRNA. Untreated cells and Lipofectamine-scrambled siRNA are used as controls. *$p<0.01$. Results were obtained from three independent experiments (n=3). Mean±SD.

The normalization of band intensity against total protein was performed using Chemidoc Image Lab™ software and the data is reported as % knock down with reference to control cells in FIG. 10. Percentage knock-down for SPARC loaded-LbL NPs is 60% and for SPARC with lipofectamine as positive control is 89%. The statistical analysis on knockdown efficiency of LbL NPs compared to blank cells, as well as scrambled-siRNA indicates significant difference (p<0.001). Hence the data indicates the reduction in the targeted protein expression by SPARC-siRNA delivered through the LbL NPs. There was no knock-down with non-specific siRNA indicating effectiveness of LbL NPs as non-viral delivery vector.

Gene Knock Down Evaluation by Western Blot

Fibroblasts (1.2×105, 2 mL) were seeded into a 6-well chamber in complete DMEM medium and cultured for 24 h, SPARC siRNA functionalized LbL NPs, lipofectamine with SPARC and scrambled-siRNA samples containing 400 pmol siRNA were treated to the cells. Cells without any treatment were used as blank cells and optimem was changed to complete DMEM medium after 24 h NPs incubation and cells were harvested, lysed after four days of incubation.

Protein extraction was carried out after preset incubation time of 96 h using cell lyses buffer, the extracted protein in each well was analyzed by using coomassi blue at 595 nm. Equivalent amount (30 µg) of protein from different samples and ladder (Precision Plus™) are loaded in to the gel. After protein separation the imaging was performed using a ChemiDoc to validate the protein separation step, further the protein transfer to the PVDF membrane was performed by using Trans-blot® (Bio-Rad) system at 200 V for about 40 min. The membranes after protein transfer were visualized in Chemidoc imager to validate the protein transfer to the membrane, further the membranes were blocked in 5% skim milk for 1 h at 20° C.

Antibody treatment was accomplished by membranes probing with primary antibody (mouse monoclonal IgG1, Santa Cruz) 1:1000 dilution in 2.5% skim milk and incubated for 1 h at 20° C., further the membrane was washed with TBST for three time intermittently at 10 min. Horseradish peroxidise linked anti-mouse secondary antibody (Jackson Immuno Labs) diluted to 1:10000 in 2.5% skim milk. The membrane with secondary antibody was incubated at 20° C. for 1 h and washed using TBST for six times intermittently at 5 min. Bands were digitally visualized using chemiluminescent substrate in ChemiDoc imager and images were captured using Quantity One software (Bio-Rad). Total protein images were obtained after protein transfer to the PVDF membrane and all the blots were normalized against control cells. For relative quantification of SPARC protein levels, band corresponding to SPARC at 43 kD was selected with triplicate runs and mean value with standard deviation is reported.

Quantitative RT-PCR Studies

To confirm that the SPARC-protein knockdown is mediated by decreased mRNA expression in FibroGRO cells, we measured the relative SPARC and RPL13 mRNA levels post 96 h LbL-SPARC and Lipofectamine-SPARC treatment (FIG. 10). The mRNA levels were reduced to 0.4±0.04 fold (relative to control or untreated cells) with LbL-SPARC NPs treated cells and is comparable to mRNA levels with Lipofectamine-SPARC treated cells. There was no reduction in mRNA levels associated with scrambled-siRNA and untreated cells, similar results were previously reported by Wong et al. (*J. Cell. Mol. Med.* 2012, 16, 1245) on knock down of SPARC protein in Human Tenon's capsule fibroblasts (HTF). The significant (p<0.01) reduction in mRNA levels on treatment with LbL NPs clearly indicates efficient delivery of SPARC-siRNA into the cells for silencing expression of the SPARC gene. Furthermore, LbL NPs are demonstrated to be effective in decreasing the mRNA levels as well as SPARC protein expression in the fibroblast cells.

The LbL nanoparticles targeting SPARC protein and reducing the mRNA levels in FibroGRO cells clearly confirm a promising approach for the use of siRNA as a therapeutic strategy for minimizing fibrosis.

In Vitro SPARC Silencing in Mouse Fibroblasts on Day 2, 7 and 14

Cell treatment with LbL concentrations: 30,000 cells per well. Treated LbL NPs: 200 ug LbL (20 uL LbL suspension) SPARC mRNA expression measured by ciPCR using the nanoparticles whereby the only negatively charged polymer was RNA as described above. The results are shown in FIG. 10 B-D.

RNA Preparation, cDNA Synthesis and Quantitative Real-Time PCR

The mRNA levels post LbL-SPARC NPs treatment were examined by plating cells in six-well tissue culture plates at a density of 120,000 cells/well in DMEM medium for 24 h. SPARC-siRNA loaded LbL NPs, lipofectamine-SPARC and Lipofectamine-scrambled siRNA each corresponding to 400 pmol of siRNA were treated to the cells and mRNA expression was evaluated four days post-treatment.

Total RNA was extracted using the RNeasy Kit (Qiagen, Singapore) according to the manufacturer's instructions. Firststrand cDNA was synthesized with 250 ng total RNA extract and 1 uL of 50 ng/µL random hexamer primer (Invitrogen Co. Singapore) with Superscript III reverse transcriptase (Invitrogen Co. Singapore) according to the manufacturer's instructions. Quantitative real-time PCR (qPCR) was performed in a total volume of 10 uL in 384-well microtiter plates. Each reaction consisted of 0.5 µL of first-strand reaction product, 0.25 µL each of upstream and downstream primers (10 µM each), 5 µL of Power SYBR Green PCR Master Mix (Applied BioSystems, CA, USA) and 4 µL of DNase-RNasefree distilled water (Sigma-Aldrich Corp., MO, USA). Amplification and analysis of cDNA fragments were carried out by use of the Roche LightCycler 480 System (Roche Diagnostics Corp, Indianapolis, USA). All PCR reactions were performed in triplicate. All mRNA levels were measured as CT threshold levels and were normalized with the corresponding 60S ribosomal protein L13' (RPL13) CT values. Values are expressed as fold increase/decrease over the corresponding values for untreated FibroGRO control cells by the $2^{-\Delta\Delta C_T}$ method. The following primers were used for RT-PCR:

```
RPL13 gene:
Forward primer
                                             (SEQ ID NO: 5)
CATCGTGGCTAAACAGGTACTG Reverse primer
                                             (SEQ ID NO: 6)
GCACGACCTTGAGGGCAGCC SPARC gene
Forward primer
                                             (SEQ ID NO: 7)
GTG CAG AGG AAA CCG AAG AG Reverse primer
                                             (SEQ ID NO: 8)
TGT TTG CAG TGG TGG TTC TG
```

Cytotoxicity Testing of Multilayer Nanoparticles xCelligence Real-Time Cell Proliferation Assay The xCELLigence system (Roche) provides real-time monitoring of cells by measuring electrical impedance across micro-electrodes integrated on the bottom of tissue culture plates. The applied 96-well electrode plate was first blanked with complete medium and subsequently $4 \times 10^3$ cells per well were seeded. LbL NPs at various amount were added to the cells, and the plate was incubated at room temperature for 30 minutes before placing into the xCELLigence instrument. Cell growth was continuously monitored for about seven days, with 25 sweeps of five minutes intervals, followed by 24 sweeps of 15 minutes interval and subsequent measurements at one hour intervals. Samples were run in triplicate and repeated three times. One representative graph of all measurements is shown.

MTT Cell Proliferation Assay $4 \times 10^3$ cells per well were seeded in 96-well plates (TPP) in complete medium and cultured overnight. Various amounts of LbL NPs (0.04-0.4 μg/μL) were added to the cells in triplicates and carefully placed in the incubator for one to seven days. MTT (5 mg ml-1, in PBS) was added at 10% of total culture volume and incubated at 37° C. for three hours. Subsequently, the solution was carefully removed from the wells and 100 μl of DMSO was added to each well. The plate was shaken gently for one hour or more to allow crystal dissolving while remaining constantly covered and kept away from direct light. Then, absorbance of each well was measured at a wavelength of 595 nm.

Figure 12:
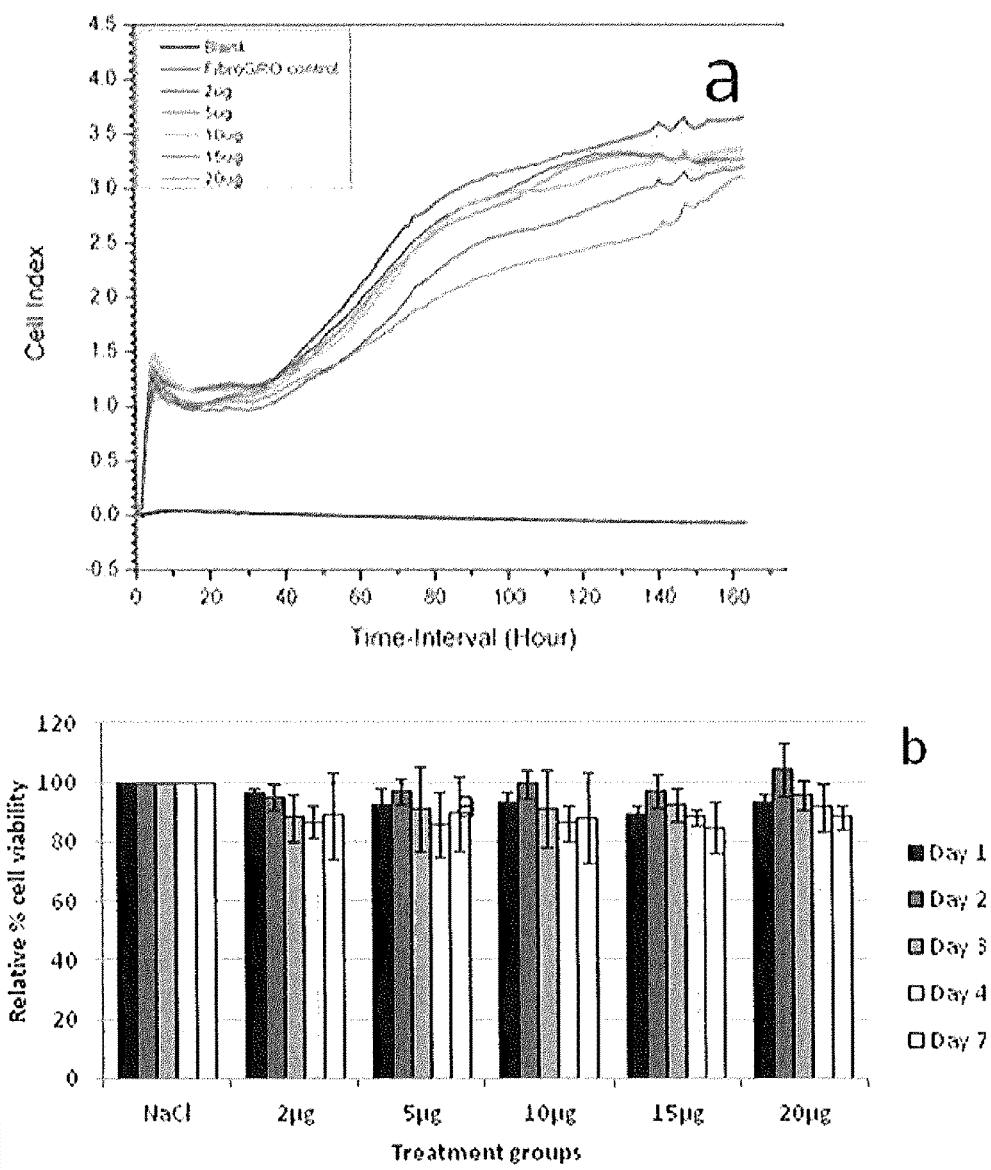
FIG. 12, The proliferation pattern of FibroGRO cells after LbL coated LbL NPs incubation. Real-time cell proliferation assays of (a) FibroGRO cells incubated with various amounts of LbL NPs are shown. Blanks (black) refer to wells with only cell culture medium. Positive controls of FibroGRO (a, red) refer to cells without LbL nanoparticle addition. (b) MTT cell proliferation assay of FibroGRO cells incubated with different amounts of LbL nanoparticles for 7 days. Varying amounts, 2, 5, 10, 15 and 20 μg of LbL NPs per well were incubated with the cells for up to 7 days and cell proliferation was monitored. Means and standard deviations of three measurements are shown.
Figure 13:
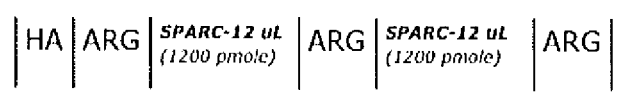
FIG. 13. In vivo delivery of siRNA into conjunctiva via nanoparticles. 5 ul of LbL nanoparticles loaded with the indicated siRNAs were injected into the mouse conjunctiva immediately after experimental surgery. The tissues were harvested on days 7 A and 14 B post-surgery and analyzed by real time-PCR for Sparc (left) and Col1a1 (right) mRNA expression. Each symbol represents a pool of tissues from 3 mice and is calculated as the ratio of expression in the operated tissues with nanoparticle injection from the left eyes relative to the paired unoperated tissues from the right eyes. Black bar indicates mean fold change for each condition. Arrow indicates direction of change with siSparc-loaded nanoparticles relative to siScram-loaded ones. Number left of arrow indicates ratio of mean fold change with siScram to that with siSparc. Number right of arrow indicates the p value comparing fold changes between siScram and siSparc nanoparticle injections.
Figure 13:
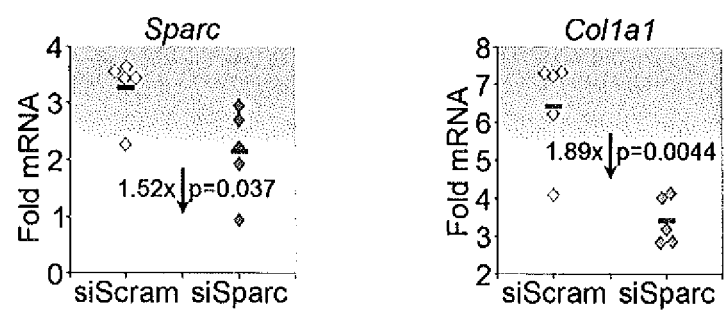
Figure 13:
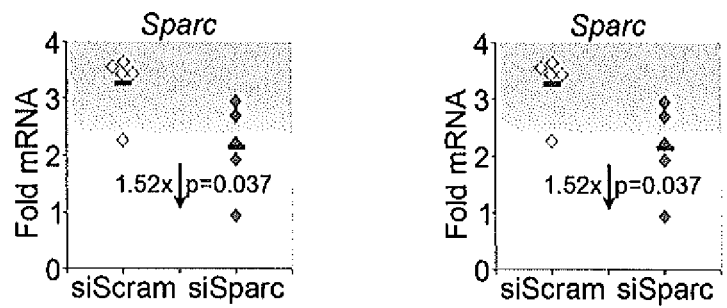

The biocompatibility and low cytotoxicity are key requirements for an acceptable siRNA delivery system, the LbL NPs were investigated in a concentration dependent study over seven days by means of xCelligence and the MTT assay, two cell proliferation methods (FIG. 12). FIG. 12a represents the biological status of FibroGRO cells without any LbL NPs as well as with increasing amounts of nanoparticles. The lower particle amounts (2 μg, 5 μg and 10 μg) displayed similar cell index values that were only slightly less than the non-treated control cells. For the higher LbL NPs amounts (15 μg and 20 μg), the cells exhibited significantly lower cell index values with the increasing amounts of nanoparticles.

The cytotoxic effects of LbL NPs towards FibroGRO cells were cross-studied with MTT assay. As observed from FIG. 12c, FibroGRO cells exhibited similar cell proliferation independent of particle amounts as already indicated by the xCelligence assay. No significant particle influence towards cell vitality can be observed for all particle concentrations for seven days. These results demonstrate the high biocompatibility of LbL NPs bases SPARC-siRNA delivery system in fibroblasts.

In Vivo Delivery of RNA to an Organism

In Vivo knockdown seen only on Day 2 with 1 siRNA SPARC layer qPCR in vivo studies demonstrated silencing of SPARC and Collagen only on Day 2. Day 7 showed significant silencing for SPARC but no silencing for Collagen. Day 10 showed no knock down for SPARC or Collagen.

Sustained knockdown requires multiple (2) layers of siRNA rather than single layer. In vivo delivery of siRNA into conjunctiva via nanoparticles. 5 μl of LbL nanoparticles loaded with the indicated siRNAs were injected into the mouse conjunctiva immediately after experimental surgery. The tissues were harvested on days 7 and 14 post-surgery and analyzed by real time-PCR for Sparc (left) and Collagen Col1a1 (right) mRNA expression. Each symbol represents a pool of tissues from 3 mice and is calculated as the ratio of expression in the operated tissues with nanoparticle injection from the left eyes relative to the paired unoperated tissues from the right eyes. Black bar indicates mean fold change for each condition. Arrow indicates direction of change with siSparc-loaded nanoparticles relative to siScram-loaded ones. Number left of arrow indicates ratio of mean fold change with siScram to that with siSparc. Number right of arrow indicates the p value comparing fold changes between siScram and siSparc nanoparticle injections.

The data shows that LbL with multiple layers of siRNA can achieve sustained knockdown in vivo.

Applications for such a system (LbL) can be used as a valuable investigative Research and Development tool in siRNA sustained delivery to target systems and diseases and also potential to develop into sustained siRNA therapeutics.

Statistics

Each experiment was repeated at least three times. All data are expressed as mean±standard deviation (SD). All values are presented as means of triplicate measurements; Statistical significance ($P<0.001$) was determined using two-tailed t-tests.

The invention claimed is:

1. A multilayered nanoparticle for delivery of RNA to a cell, the nanoparticle comprising: a core nanoparticle coated by alternating positively and negatively charged polymer layers, wherein the number of layers is 2 or more and wherein at least one of the negatively charged polymer layers comprises RNA; wherein the RNA is an siRNA having a nucleotide sense sequence as set forth in SEQ ID NO:1 and a nucleotide antisense sequence set forth in SEQ ID NO:2.

2. The multilayered nanoparticle according to claim 1, wherein the negatively charged polymer layer comprises siRNA or each of the negatively charged polymer layer comprises siRNA and is sandwiched between two positively charged polymer layers.

3. The multilayered nanoparticle according to claim 1, wherein the positively charged polymer is a polycation or comprises poly (L-arginine).

4. The multilayered nanoparticle according to claim 1, wherein the negatively charged polymer is a polyanion or comprises dextran sulphate.

5. The multilayered nanoparticle according to claim 1, further comprising a targeting peptide or targeting protein as an outermost layer.

6. The multilayered nanoparticle according to claim 1, wherein the nanoparticle core is biocompatible or biodegradable.

7. The multilayered nanoparticle according to claim 1, wherein the nanoparticle core comprises hydroxyapatite, calcium carbonate, silica, poly(lactic acid) (PLA), or combinations thereof.

8. The multilayered nanoparticle according to claim 1, wherein the nanoparticle core comprises a liposome.

9. The multilayered nanoparticle according to claim 1, wherein the nanoparticle core is negatively charged.

10. The multilayered nanoparticle according to claim 1, wherein the multilayered nanoparticle comprises 3 to 10 layers.

11. The multilayered nanoparticle according to claim 1, wherein an outermost layer comprises poly(L-arginine).

12. The multilayered nanoparticle according to claim 1, wherein the multilayer comprises at least 2 negatively charged polymer layers comprising siRNA.

13. The multilayered nanoparticle according to claim 1, wherein the siRNA targets a Secreted Protein, Acidic and Rich in Cysteine (SPARC) gene.

14. A method for manufacturing a multilayered nanoparticle comprising a core nanoparticle coated by alternating positively and negatively charged polymer layers, wherein the number of layers is 2 or more and wherein at least one of the negatively charged polymer layers comprises RNA, wherein the RNA is an siRNA having a nucleotide sense sequence as set forth in SEQ ID NO:1 and a nucleotide antisense sequence set forth in SEQ ID NO:2,
the method comprising the steps of:
  a. Providing a nanoparticle core;
  b. Contacting the nanoparticle core with a positively charged or negatively charged polymer to form a first polymer layer on the nanoparticle core;
  c. Contacting the coated nanoparticle of step b) with a polymer charged opposite to that used in step b) to form a second polymer layer on the nanoparticle;
  d. Optionally repeating steps b) and c).

15. A method for delivering RNA to a cell or organism, the method comprising: contacting said cell or organism with an effective amount of a multilayered nanoparticle comprising a core nanoparticle coated by alternating positively and negatively charged polymer layers, wherein the number of layers is 2 or more and wherein at least one of the negatively charged polymer layers comprises RNA, wherein the RNA is an siRNA having a nucleotide sense sequence as set forth in SEQ ID NO:1 and a nucleotide antisense sequence set forth in SEQ ID NO:2.

16. A method for treating an RNA-treatable disease or disorder in a subject, the method comprising administering to the subject an effective amount of a multilayered nanoparticle comprising a core nanoparticle coated by alternating positively and negatively charged polymer layers, wherein the number of layers is 2 or more and wherein at least one of the negatively charged polymer layers comprises RNA, wherein the RNA is an siRNA having a nucleotide sense sequence as set forth in SEQ ID NO:1 and a nucleotide antisense sequence set forth in SEQ ID NO:2.

17. The method according to claim 16, wherein the siRNA inhibits Secreted Protein, Acidic and Rich in Cysteine (SPARC) expression and the RNA-treatable disease or disorder is scarring and said treatment reduces scarring in the subject.

18. The method according to claim 17, wherein the multilayered nanoparticle is administered to the conjunctiva after eye surgery.

* * * * *